(12) United States Patent
Watanabe

(10) Patent No.: US 6,275,287 B1
(45) Date of Patent: Aug. 14, 2001

(54) CHECK DETECTOR FOR GLASS BOTTLE NECK AND FINISH PORTION

(75) Inventor: Tsukasa Watanabe, Hyogo (JP)

(73) Assignee: Nihon Yamamura Glass Co., Ltd., Hyogo (JP)

( * ) Notice: Subject to any disclaimer, the term of this patent is extended or adjusted under 35 U.S.C. 154(b) by 0 days.

(21) Appl. No.: 09/295,703

(22) Filed: Apr. 21, 1999

(30) Foreign Application Priority Data

Apr. 25, 1998 (JP) .................................................. 10-131176

(51) Int. Cl.$^7$ .................................................... C01N 21/90
(52) U.S. Cl. ........................................ 356/239.4; 356/428
(58) Field of Search ............................ 356/239.4, 239.5, 356/240.1, 428; 250/223 B

(56) References Cited

U.S. PATENT DOCUMENTS

| | | | |
|---|---|---|---|
| 4,293,219 | * 10/1981 | Ducloux | ................................ 356/240 |
| 4,650,326 | 3/1987 | Nagamine et al. . | |
| 4,701,612 | 10/1987 | Sturgill . | |
| 5,020,908 | * 6/1991 | Hermann | ............................... 356/239 |
| 5,900,945 | * 5/1999 | Hinata et al. | ......................... 356/428 |

FOREIGN PATENT DOCUMENTS

| | | |
|---|---|---|
| 222959 | 5/1987 | (EP) . |
| 763727 | 3/1997 | (EP) . |
| 2087549 | 10/1981 | (GB) . |
| 4294262 | 10/1992 | (JP) . |

* cited by examiner

Primary Examiner—Richard A. Rosenberger
(74) Attorney, Agent, or Firm—Price and Gess

(57) ABSTRACT

A check detector for the neck and finish portion of glass bottles is disclosed. The check detectors comprises means for rotating glass bottles successively conveyed to a fixed position and a slide block which can change position freely in the width direction and vertical direction of the bottle. A plurality of light emitters for illuminating the neck and finish potion of the glass bottle are mounted to the slide block. The light by from the plurality of the light emitters is converged to the illuminated region from difference directions, and there are a plurality of light receivers equipped with light sensors for detecting the light reflected by checks in the neck and finish portion of the bottle, the light reflected by the mold seam formed at the neck and finish portions, and the directly transmitted light passing through the neck and finish portion, via lenses mounted to the slide block. There is a light emitter control section for constantly operating a plurality of light receivers in the light emitting condition so that the reflected and direct light are input as data, wherein each of the light receiving elements are divided so as to correspond to the vertical position of the neck and finish portion. The data inputted as light reflected at the seam and the data inputted as the direct light transmitted through the neck and finish portions are deleted.

12 Claims, 16 Drawing Sheets

CHECK DETECTOR FOR GLASS BOTTLE NECK AND FINISH PORTION

BACKGROUND OF THE INVENTION

1. Field of the Invention

The present invention relates to a check detector for glass bottle neck and finish portion.

2. Description of the Prior Art

In manufacturing glass bottles, there are cases in which so-called checks like cracks or seeds and blisters are generated in the wall thickness of the neck and finish portion.

For the seeds and bisters, no problem is caused in the viewpoint of products when they are small, but since the checks are critical defects that would result in breakage of glass bottles, the presence of checks is optically detected.

There are many types of checks that can be generated in a glass bottle neck and finish portion, such as those generated in simple threaded necks and necks for crown caps. For example, in the simple threaded neck and finish, several types of checks such as vertical, horizontal, and other checks may exist, but to optically detect the presence of these checks by types, the following method was conventionally used. That is, in the course of the handling route the, transfer of the glass bottles was intermittently stopped and with glass bottles rotated at the stopped position, a light emitter for emitting the neck and finish portion of the rotating glass bottle with light was located in the width direction on one side of the handling route, while a light receiver for detecting the reflected light totally reflected at the checks at the glass bottle neck and finish portion was located on the other side in the width direction of the handling route, and based on an output when the light receiver received the reflected light, the existence of, for example, vertical checks was detected.

Now, since the checks are generated without any directionality, checks must be detected with the following points taken into account. That is, ① there is a boundary of reflection because checks shine due to total reflection, and ② there is a case in which reflected light due to checks may not exit to the outside.

Consequently, hitherto, in order to improve the detection accuracy in detecting the presence of, for example, vertical checks, one each of light emitter and light receiver is paired, and a plurality of pairs of emitters and receivers are installed. And by varying the light emitting direction of the emitter and light receiving direction of the receiver for each pair and at the same time giving consideration to the arrangement of a plurality of pairs for easy detection of vertical checks, detection of vertical checks is able to be carried out under various optical conditions.

However, there are still the following problems:

① because there are extremely many combinations of emitters and receivers, the detector directly detects even the light transmitting through the neck and finish portion if detection is carried out at one place only, and ② total reflections other than vertical checks are also detected. For example, reflected light which is totally reflected at the mold seam formed at the glass bottle neck and finish portion is also detected, and there is a case in which non-defective glass bottles may be judged defective.

③ when a plurality of emitters are simultaneously lighted, that is, when emitting beam is simultaneously emitted from multiple directions, the emitting beams interfere with one another, degrading the detection ratio, and at the same time, small seeds and bisters generated in the neck and finish portion excessively reflect, resulting in degraded detection accuracy. And for the corrective actions, turning off part of the emitters and receivers as required among a plurality of pairs of emitters and receivers, or degrading the detection sensitivity may eliminate the combination required for essential vertical check detection, resulting in degraded detection ratio.

By the way, the present applicant proposed a check detector of a glass bottle neck and finish portion with emitters and receivers arranged and suited for vertical checks detection (Publication of Unexamined Patent Application No. Hei 4-294262) but even if the above-mentioned problems may be able to be overcome, (A) the results obtained by arrangement of a plurality of pairs were to detect the presence of vertical checks. That is, for example, vertical checks at the top (upper vertical checks), vertical checks at the intermediate portion (middle vertical checks), vertical checks at the bottom (lower vertical checks), etc. generated in this order at the top, middle, and bottom positions of the neck and finish portion were unable to be identified and detected.

In addition, (B) because, vertical checks were unable to be sorted unless influences of noises contained in detection signals taken into the receiver were reduced, the data corresponding to the detection signal must be differentiated at the signal processor mounted at the stage after the receiver. That is, because the detection signal has an inclination corresponding to the signal of vertical checks for each vertical check appearing in the above-mentioned data, it is necessary to perform processing to remove the noise by carrying out time differentiation and to leave vertical check signals only.

SUMMARY OF THE INVENTION

Under these circumstances, it is a main object of this invention to provide a check detector of a glass bottle neck and finish portion that can improve the check detection accuracy by positively reducing rejection of non-defective glass bottles.

In order to achieve this object, this invention is characterised by being comprised of a glass bottle rotating unit for rotating a glass bottle successively conveyed to a fixed position and around the glass bottle in the course of glass bottle handling route, a slide block which can change position freely in the width direction and vertical direction of the handling route, a plurality of light emitters for emitting light to the neck and finish portion of the glass bottle as it is rotated at the fixed position with light mounted to the slide block, while the emitted region of the emitting light by a plurality of the light emitters is fixed to one position and the relevant emitting light is converged to the emitted region from directions which differ one another, a plurality of light receivers equipped with light receiving sensors for detecting the reflected light reflected at the checks generated at the neck and finish portion, the reflected light reflected at the molds seams formed at the neck and finish portion, and direct light transmitted through the neck and finish portion via lenses mounted to the slide block, a light emitter control section for switching a plurality of the light emitters successively and repeatedly in the light emitting condition, and a light receiver control section for constantly operating a plurality of light receivers in the light emitting condition so that each of the reflected lights and direct light are inputted as data, wherein each of the light receiving sensors is composed with diode arrays comprising a plurality of light receiving elements divided in advance so as to correspond to the vertical position of the neck and finish portion and at the same time, the data inputted as reflected light reflected at the seam and the data inputted as the direct light for transmitting through the neck and finish portion are intended to be deleted, respectively.

By the above-mentioned characteristic configuration, when, for example, vertical checks at the glass bottle neck and finish portion are detected, a plurality of emitters are switched successively to the light emitting condition and emitting beams are emitted toward the glass bottle neck and finish portion from a plurality of different directions to one place of the emitted region, the detected portion, and the presence of the vertical checks is thereby able to be detected simultaneously at many places.

That is, as shown in FIG. 1 and FIG. 3, the emitted region S of emitting beam L by a plurality (for example, 12 pieces) of emitters 21–32 is fixed to one place for the neck and finish portion 1 of a glass bottle 3 which rotates in an R direction at a fixed position, and the relevant emitting beams L are converged to the emitted region S from different directions. For example, emitters 21–32 are repeatedly switched instantaneously to the light emitting condition throughout 360° successively one by one in the lighting timing, for example, as shown in FIG. 7 while the glass bottle 3 is continuously rotated around the glass bottle center P in the check detection section D (see FIG. 4).

The twelve emitting beams are emitted successively to the position of the neck portion 1 which is superimposed on the emitted region S from a plurality of directions different from one another to the emitted region S each time. In such event, if the emitted region S is set to, for example, a rectangular form and the lateral width X (emitted width) of the emitted region S is set to 5 mm, the lighting timing is switched for every 1 mm pitch of the circumferential length. That is, because the emitted width X is set to be greater than the circumferential length on which the glass bottle 3 rotates to move, emitting beams L can be emitted to the neck and finish portion 1 of the glass bottle 3 free of unemitted portions on the neck and finish portion 1 of the glass bottle 3 which passes the emitted region S. In FIG. 1 and FIG. 3, character Y designates the vertical length of the rectangular emitted region S.

A first vertical check detection is carried out, for example, at the lighting timing clock $a_1$ –$a_{12}$ shown in FIG. 7 and the data is collected from this detection area for processing. Then, when the next detection area in the neck and finish portion 1 is superimposed on the emitted region S, the second vertical check detection is carried out at the lighting timing clock $b_1$–$b_{12}$, and the data is collected from this detection area for processing. Thereafter, in a similar manner, the data is collected and processed throughout one circumference of the neck and finish portion 1 of the glass bottle 3.

In this invention, since the successive light emitting system is adopted in place of a simultaneous light emitting system for the lighting timing of the emitting beam by the emitter as described above, it is possible to avoid the situation in which emitting beams interfere with one another to lower the detection ratio or small seeds and bisters generated at the neck and finish portion excessively shine to degrade the detection accuracy. In FIG. 3, numerals 51 through 58 designate a plurality of light receivers (cameras).

In addition, in this invention, it is also possible to solve any inconvenience arising from the constantly turning on of all the receivers 51–58 in the light emitting condition. For example, it is possible to avoid the inconvenience of judging non-defective glass bottles defective by allowing receivers 51–58 to catch not only the reflected lights reflected at, for example, vertical checks but also reflected lights reflected at the seam and even direct lights transmitting through the neck and finish portion when the seam reaches the emitted region S as the glass bottle rotates.

That is, since this invention is configured to delete the data taken in as reflected lights reflected at the seam and the data taken in as direct lights transmitting the neck and finish portion, the above-mentioned inconvenience can be positively solved and this also enables an accurate vertical check detection.

Furthermore, since each of the light receiving sensors 2 which receivers 51–58 possess is configured with diode arrays comprising a plurality of light-receiving elements 11–18 divided in advance in such a manner to correspond to the vertical position of the neck and finish portion, even the contents of the check can be identified and detected.

That is, in FIG. 1, when upper vertical check a, middle vertical check b, and lower vertical check c are generated in this order at the top, intermediate, and bottom positions superimposed on the emitted region S, with a conventional check detector, the presence of vertical checks only is judged and a selection of the top vertical check a, middle vertical check b, and lower vertical check c was not possible, but in this invention, in FIG. 1 and FIG. 2, for example, of a plurality of light receiving elements 11–18 in the light receiving sensor 2 of the light receiver 53, the reflected light A totally reflected at the upper vertical check a is received, for example, by a light receiving element 18 and the reflected light B totally reflected at the middle vertical check b is received at a light receiving element 14, and the reflected light C totally reflected at the lower vertical check c is received at a light receiving element 11. Consequently, the upper vertical check a, middle vertical check b, and lower vertical check c can be identified and detected.

Consequently, for example, 12 pieces of emitters 21–32 used in this invention are configured, respectively, as an emitter 31 indicated in FIG. 2, by installing a plurality of light emitting diodes (LED) 60, a converging lens system 61 containing a condenser lens, and a slit 62 intermediately installed to the lens system 61 in a pair of separable cylindrical boxes 63, 63.

For receivers 51–58 according to this invention, diode array cameras are used. The diode array cameras 51–58 comprise a light receiving sensor 2 comprising a diode array composed of a plurality of light receiving elements 11–18, a cylindrical box 66 with a hole 65 for allowing reflected lights A, B, C, to pass, and a light converging lens system 64, respectively. This light converging lens system 64 is installed in the box 66 in such a manner that the system receives the reflected lights A, B, C and the reflected light A is received by the light receiving element 18, the reflected light B by the light receiving element 14, and further the reflected light C by the light receiving element 11.

And since a plurality of light receiving elements 11–18, divided in advance, are installed to correspond to the vertical position of the neck portion 1 and signal outputs of diode array cameras 51–58 are parallel, a high-speed response can be obtained. In such event, it is desirable to divide the light receiving elements 11–18 into eight parts and to configure for 8-bit data processing in order to detect the defect existing position of the glass bottle neck and finish portion more accurately.

Furthermore, since the light receiving surface of each light receiving sensor 2 is composed with divided light receiving elements 11–18 in this invention, the noise region can be made smaller. Consequently, the differentiation processing of the data corresponding to the detection signal taken in by the receiver as in the case of conventional check detectors is no longer required.

DETAILED DESCRIPTION OF THE PREFERRED EMBODIMENTS

Figure 1:
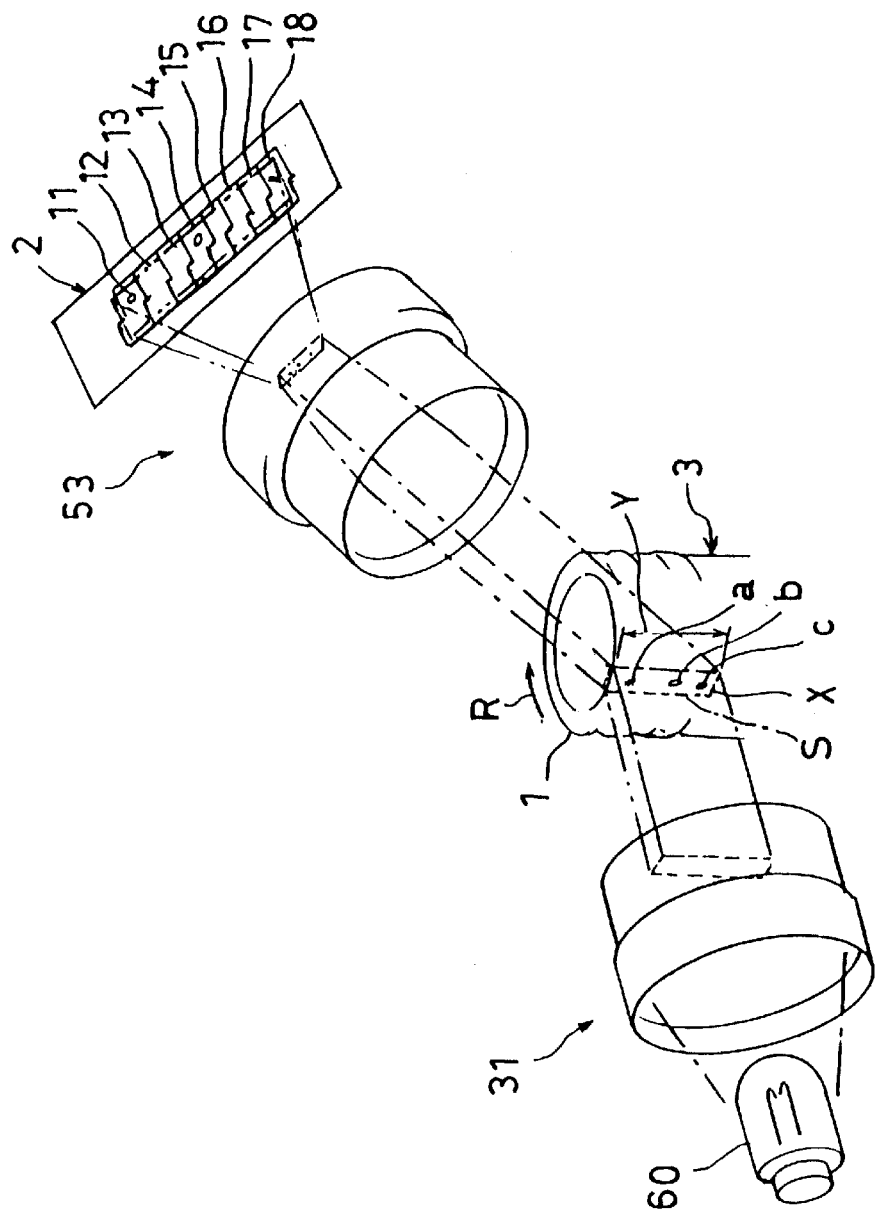
FIG. 1 is a perspective view for explaining the optical principle of one embodiment according to the present invention.

Referring now to the drawings, preferred embodiments according to the invention will be described in detail hereinafter.

Figure 2:
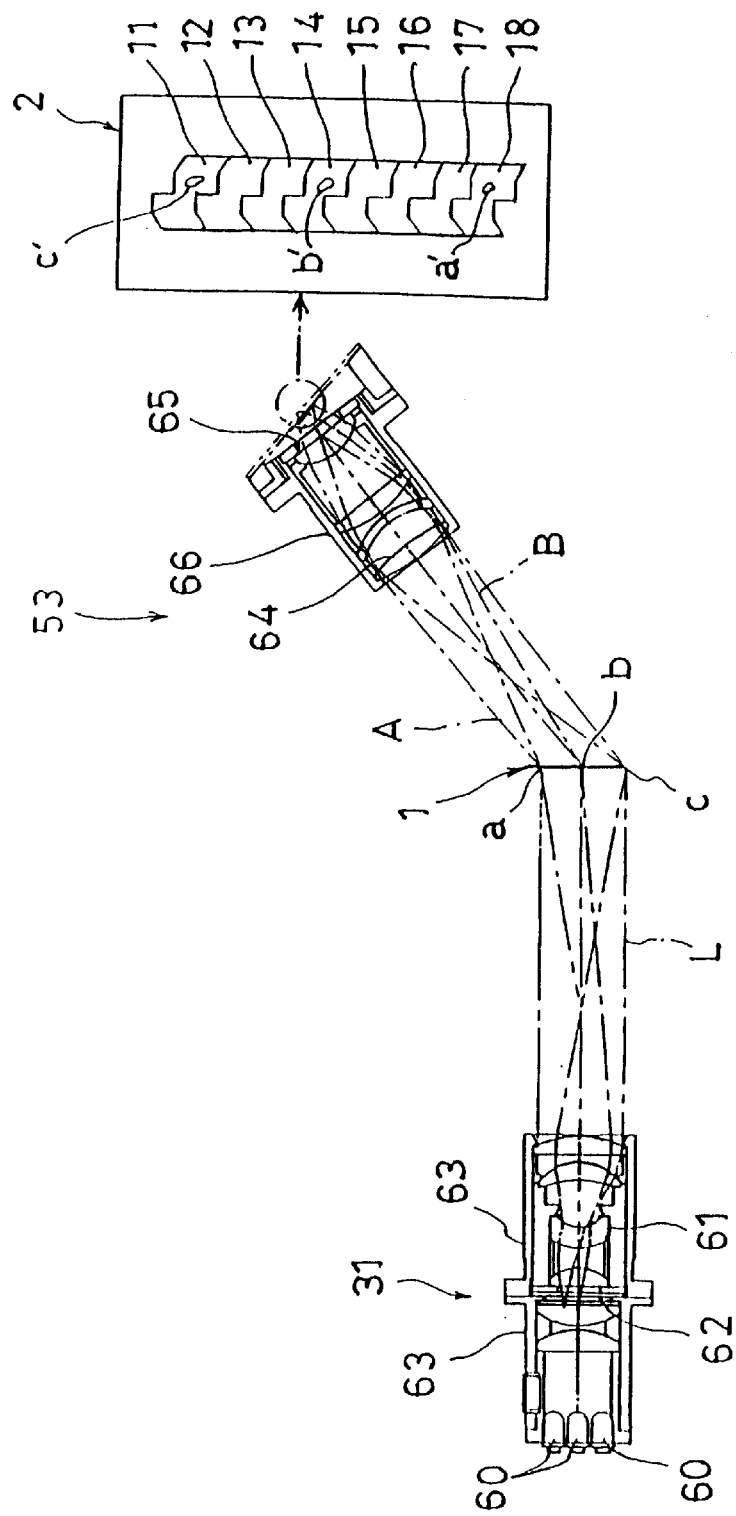
FIG. 2 is a block diagram for explaining the optical principle in the embodiment.

FIG. 1 and FIG. 2 are illustrations for optical principle used of the carrying out a detection of the presence of, for example, an upper vertical check a, a middle vertical check b, a lower vertical check c, etc., while FIG. 3 through FIG. 6 show the details of the check detector.

In FIG. 1 through FIG. 6, a glass bottle 3, taken out successively from a conveyor by an infeed wheel not illustrated, is intermittently transferred by a main star wheel 33 and conveyed successively to a check detection section D. The detected glass bottle 3 is returned to a conveyor 1 via a take-out wheel by the star wheel 33. The star wheel 33 is equipped with a rotating shaft to which two wheel plates 34 with glass bottle introducing sections formed on the circumference are mounted at suitable intervals.

Numeral 35 is a glass bottle rotating means comprising a turntable 36 and a motor 37 and is mounted to a check detection section D.

The star wheel 33 is configured to intermittently stop the drive every time the glass bottle introducing section is located at a position that corresponds to the turntable 36, and is configured to rotate the glass bottle 2 around the glass bottle center P at a fixed position while the star wheel 33 makes an intermittent drive stop.

Figure 8:
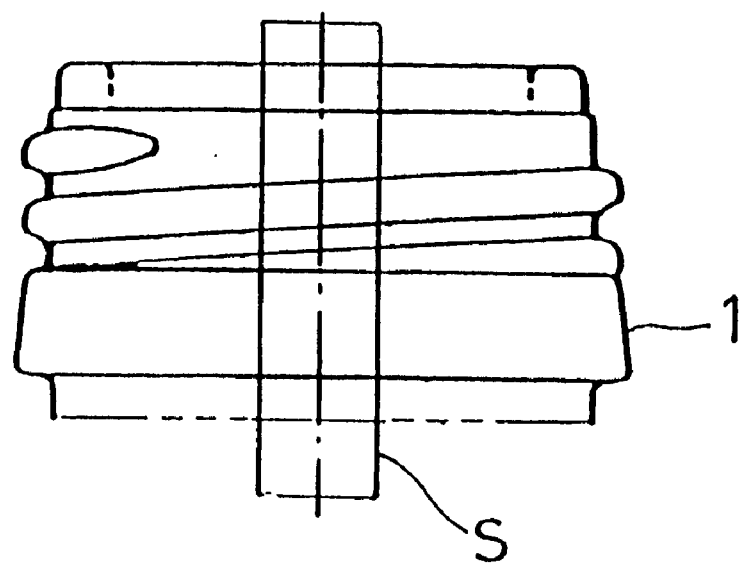
FIG. 8 is a block diagram showing the glass bottle neck and finish portion used in the embodiment.

Numeral 38 is a check detector of the neck and finish portion 1 of the glass bottle 3 arranged at the check detection section D, comprising a post 40 equipped with an elevating member 39 which is free to change the position and free to be fixed in the vertical direction and erectly mounted to the outside of the glass bottle handling route by the star wheel 33, a horizontal guide 41 extendedly equipped to the elevating member 39 in the condition to allow it to cross the glass bottle handling route, a slide block 42 equipped along the horizontal guide 41 in such a manner as to be free to change the position and free to be fixed, and a plurality of emitters 21–32 configured as described above and receivers 51–58 which function as diode array cameras as described above, both mounted to the slide blocks 42, respectively. In this embodiment, emitters 21–32 and receivers 51–58 are arranged face to face so that vertical checks a, b, c can be easily detected. In this embodiment, for the inspected neck and finish portion 1, the most popular simple threaded type for pilfer-proof cap is employed as shown in FIG. 8.

Specifically, an emitter bracket 43 is mounted, respectively, on one side of the glass bottle handling route in the width direction with a specified angle provided with respect to the slide block 42, and at the same time, emitters 21–32 are mounted to each bracket 43 so that emitting light L can be emitted from obliquely above, from obliquely below, and from the horizontal direction to the outside of the neck and finish portion 1 of the glass bottle 3 rotated at the fixed position, and the emitting light L by a plurality of the emitters 21–32 is converged to the emitted region S which is superimposed on the neck and finish portion 1.

Figure 3:
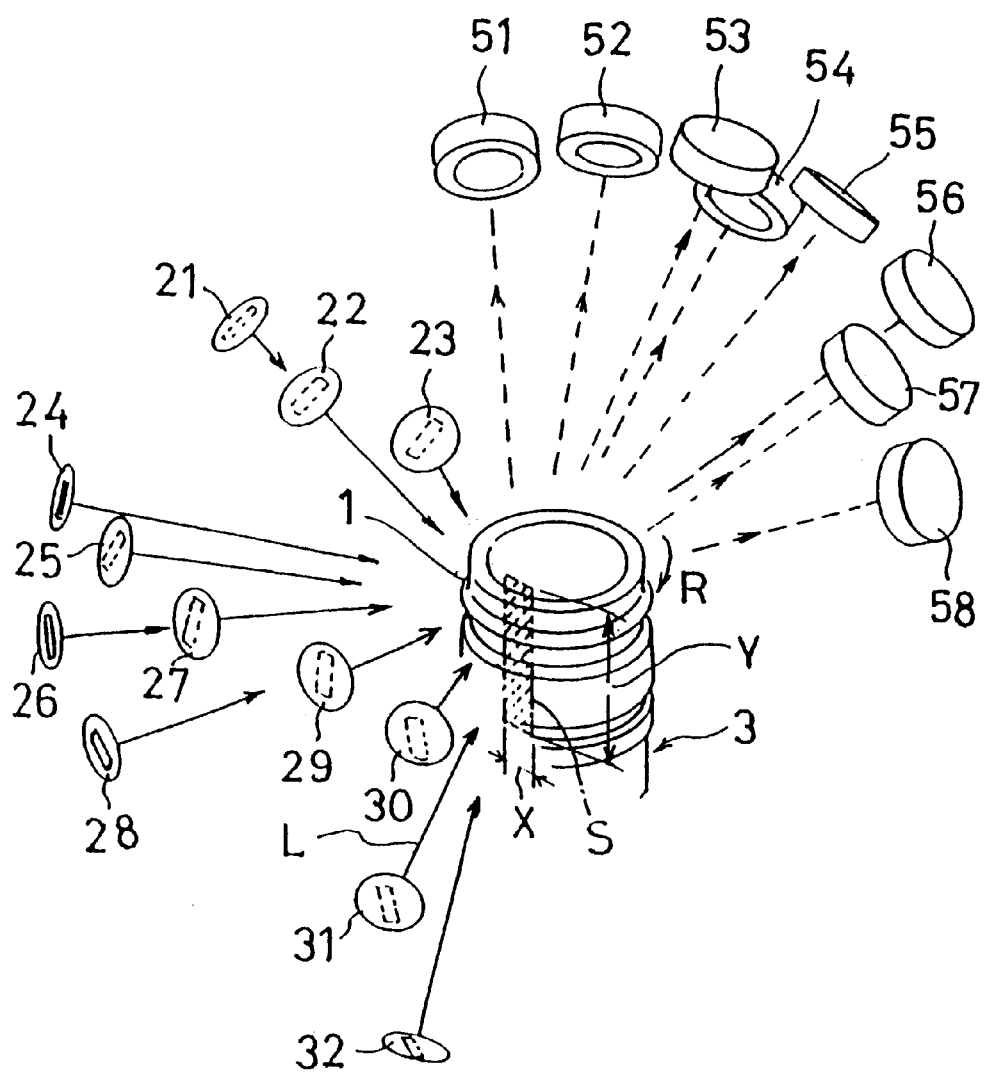
FIG. 3 is a perspective view for explaining the path of the emitting and receiving light to the neck and finish portion of a glass bottle in the embodiment.
Figure 4:
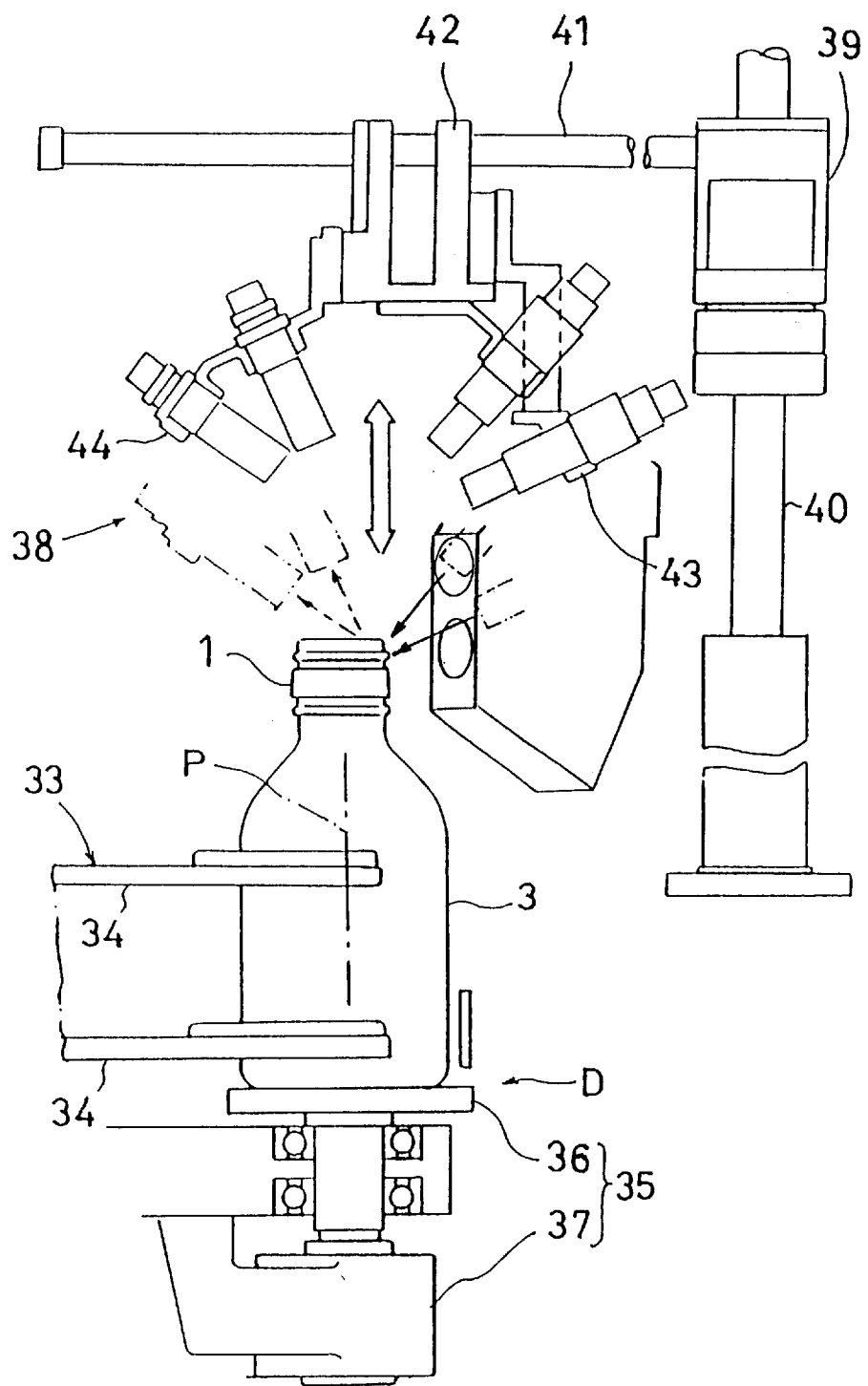
FIG. 4 is a full view of a check detector of the glass bottle neck and finish portion of the embodiment.
Figure 5:
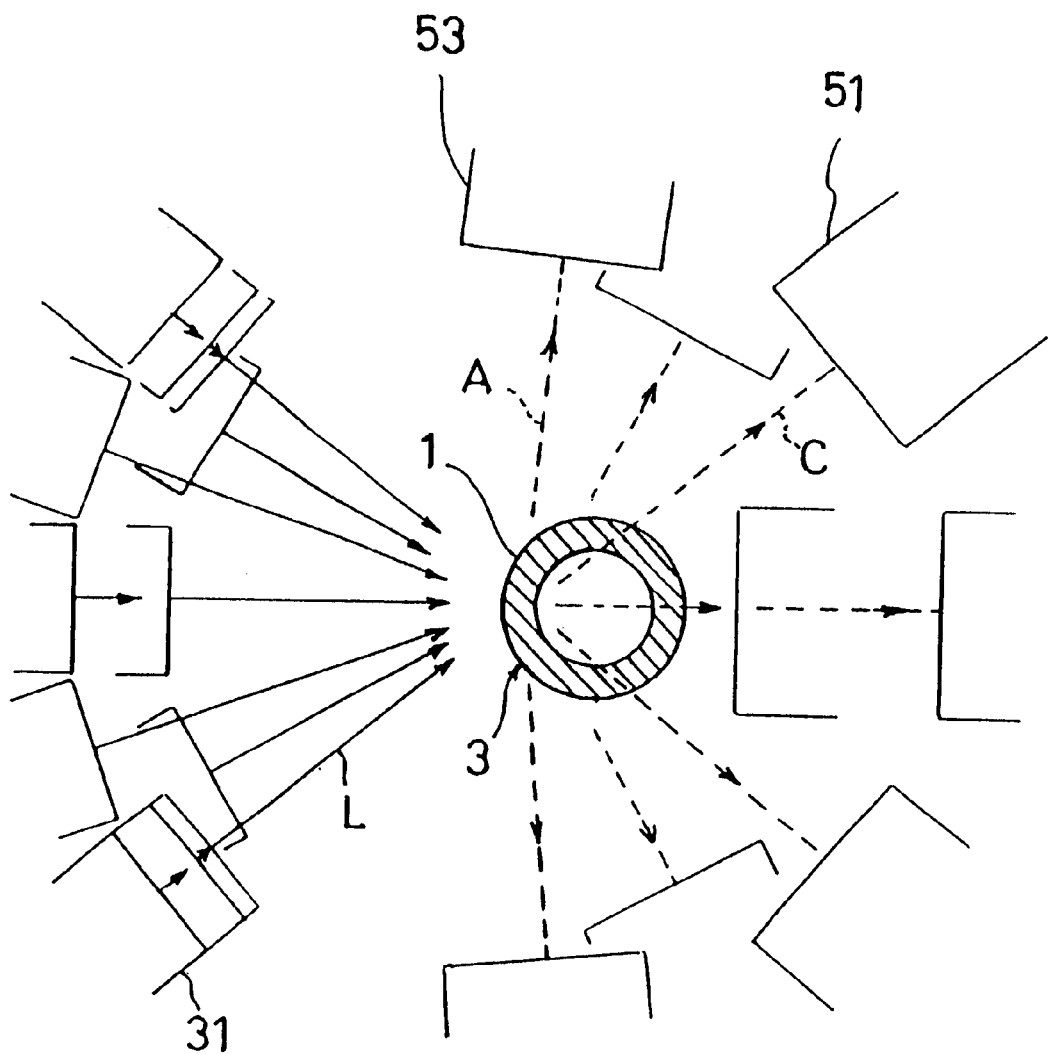
FIG. 5 is a plane view for explaining the path of the emitting and receiving light to the neck and finish portion of a glass bottle in the embodiment.
Figure 6:
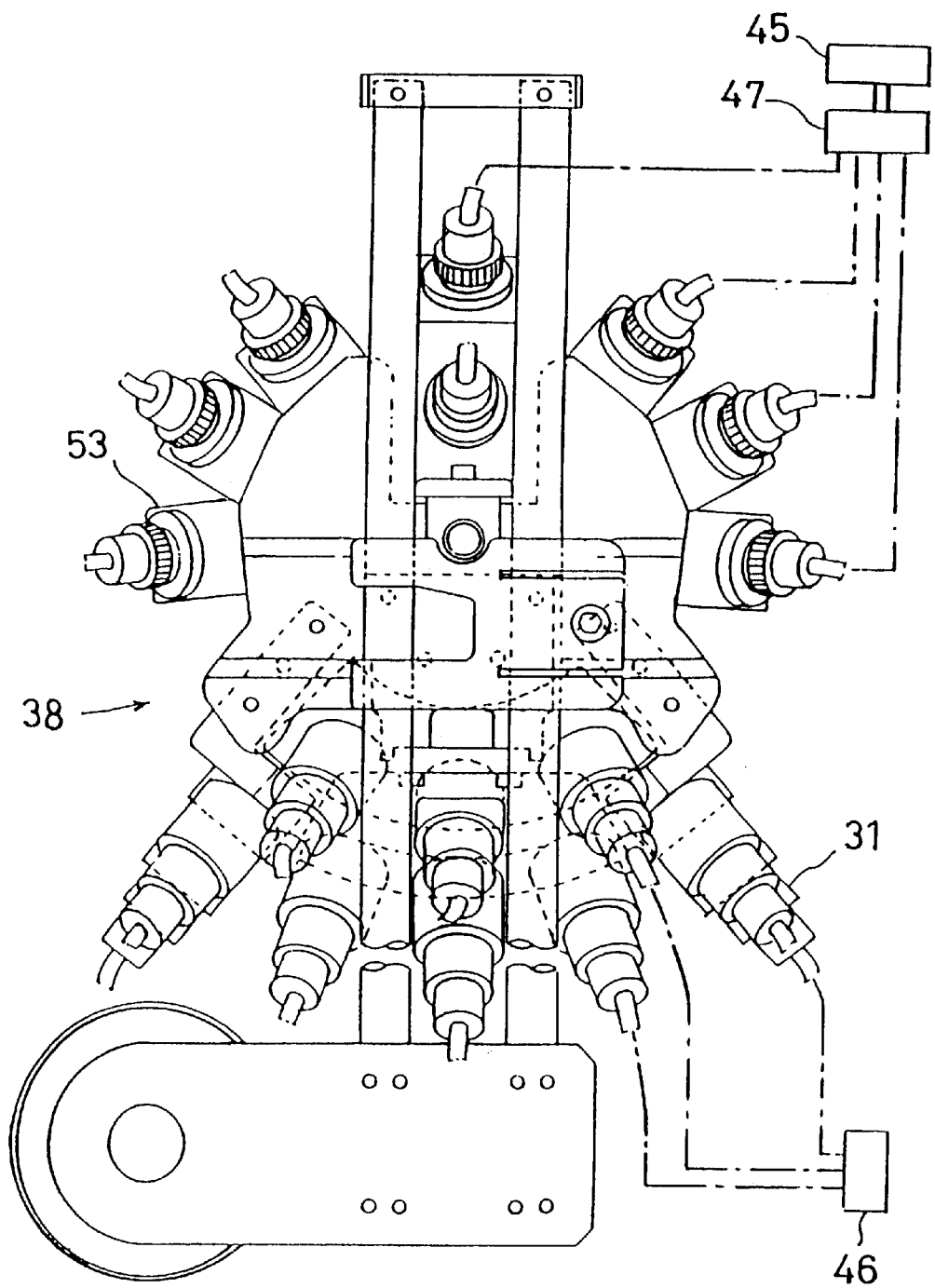
FIG. 6 is a plane view of a check detector of the glass bottle neck and finish portion of the embodiment.

More specifically, in FIG. 3 and FIG. 5, for example, of the 12 emitters 21–32, the light emitting direction of two emitters 28, 32 is directed obliquely above, that of the two emitters 26, 31 directed nearly to horizontal direction, and that of the remaining emitters directed obliquely below.

On the other hand, on the other side of the glass bottle handling route in the width direction with respect to the slide block 42, for example, 8 receivers 51–58 are mounted. In such event, the receiver bracket 44 is mounted, respectively, with the specified angle provided, and at the same time, receivers 51–58 are mounted to each bracket 44 so that the reflected light reflected at the neck and finish portion 1 can be detected. The receivers 51–58 are mounted to each bracket 44 independently or in a pair.

Numeral 45 is a unit for detecting the presence on checks of the neck and finish portion 1, and detects the presence of an upper vertical check a, a middle vertical check b, and a lower vertical check c at the neck and finish portion 1 based on the quantity of light caught by receivers 51–58. Numeral 46 is an emitter control section for switching emitters 21–32 successively one by one to the repeated emitting condition.

Numeral 47 is a receiver control section and constantly operates all the receivers 51–58 in the emitting condition so that the reflected lights A, B, C reflected at the vertical checks a, b, c are inputted as data $D_1$ if any of the above-mentioned vertical checks a, b, c is generated. Consequently, reflected light reflected at the mold seam formed at the neck and finish portion 1 and direct light transmitting through the neck and finish portion 1 are inputted also as data $D_2$, $D_3$, respectively.

And in this invention, because all the receivers 51–58 are brought to the light detecting condition, a masking operation is able to be carried out from the detection monitor screen in order to prevent inconvenience in that even the reflected light reflected at the seam and the direct light transmitting through the neck and finish portion 1 are caught by the receivers 51–58 and the check presence detecting unit 45 judges the non-defective glass bottle 3 defective, even though the seam is not a check.

For example, mask data M is created in advance for deleting the two types of data $D_2$, $D_3$, respectively. And masking operation is carried out by superimposing the mask data M on the inputted data $D_1$, $D_2$, $D_3$ by combinations of emitters 21–32 with receivers 51–58 which appear on one screen of the detection monitor during operation of the check detector 38 so that the check presence detecting unit does not process the glass bottle as defective with the reflected light from the seam.

For example, a non-defective glass bottle which has no check at the neck and finish portion 1 and has a seeds, blister at the seam that causes no problem as a product is set to the check detector 38, and the inspected portions with the worst condition of the relevant glass bottle are emitted successively with the emitting light, and in such event, combinations of emitters and receivers subject to the reflected light are looked over, and which combinations of receivers react with the seam is confirmed. On the other hand, which combination of receivers react with direct light is also confirmed and the mask data M is created. With this contrivance, the two types of data $D_2$, $D_3$ can be deleted by the masking operation from the detection monitor screen.

Figure 7:
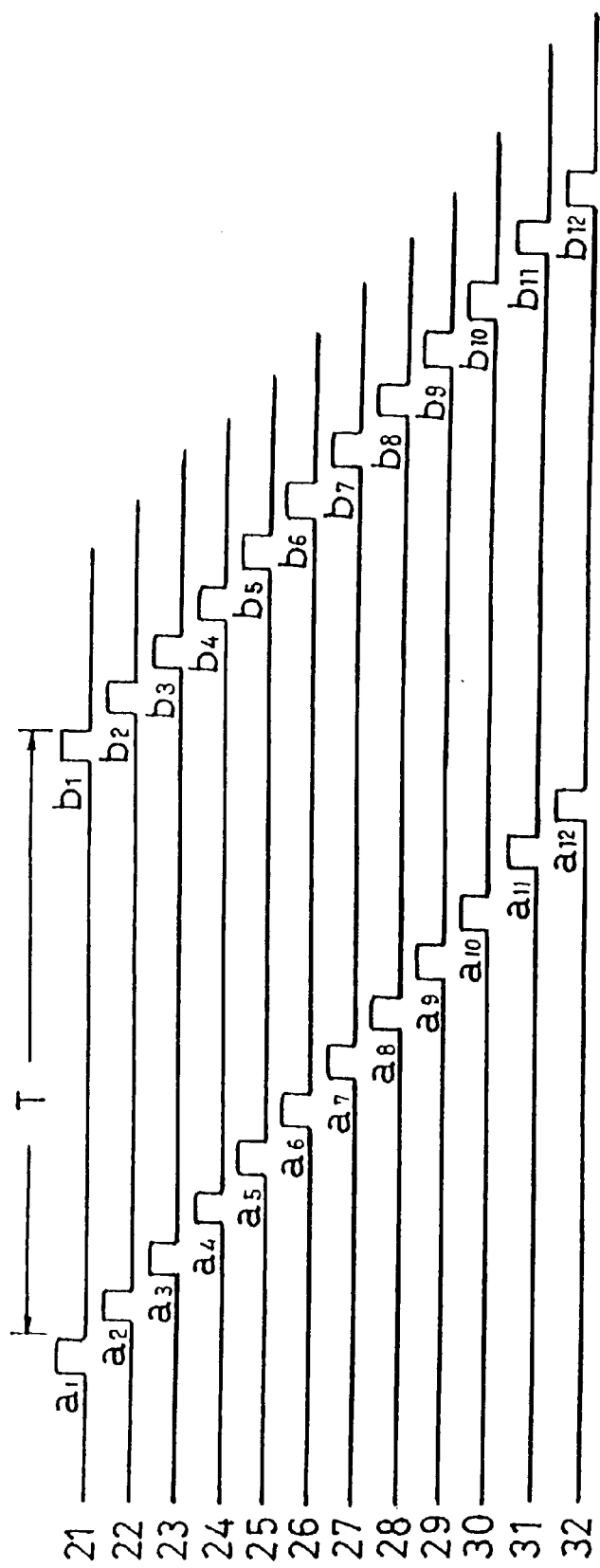
FIG. 7 is an illustration showing a light emitting timing table of an emitter in the embodiment.

In addition, in this invention, because light receiving elements 11–18 of each light receiving sensor 2 of light receivers 51–58 are divided into 8 parts to enable 8-bit data processing, signal outputs of diode array cameras 51–58 are parallel and high-speed response is able to be obtained. That is, this invention intends to inspect the presence of, for example, upper vertical check a, middle vertical check b, and lower vertical check c by the lighting timing (see FIG. 7) of emitters 21–32 and the signal analysis of combinations of receivers 51–58, which function as diode array cameras, but since it is able to dispatch the signal outputs to the data processor by 8 data buses, the invention has an advantage to shorten the data transfer time not only over a light receiving sensor used in the conventional art but also as a light receiving sensor as compared to a CCD which carries out data processing by 1 bit.

With the above configuration, instantaneously switching a plurality of emitters 21–32 to the light emitting condition successively one by one, for example, at every 1 mm pitch of circumferential length while a glass bottle 3 is continuously turned to make one rotation around the glass bottle center P in the check detection section D, that is, emitting light to the neck and finish portion 1 of the glass bottle without any blank, is repeatedly carried out throughout 360°, and the neck and finish portion 1 is emitted with emitting light from a plurality of directions which differ from one to another. That is, in carrying out a check detection, emitting light L from emitters 21–32 is directed to the outer surface of the neck and finish portion and the emitting light L is converged to one place S from a plurality of directions which differ from one another, and the neck and finish portion 1 that corresponds to the 1 mm pitch of circumferential length that is transmitting the one position S is continuously emitted with emitting light L successively one by one from emitter 21 to emitter 32, and to prevent any blank of light emission, the following neck and finish portion 1 which corresponds to 1 mm pitch of circumferential length is continuously emitted with emitting light L one by one from emitter 21 to emitter 32 while the neck and finish portion passes the one place S, and this operation is repeatedly carried out for 360°.

And if the upper vertical check a, middle vertical check b, and lower vertical c exist in the neck and finish portion 1, reflected lights A, B, C from the relevant vertical checks a, b, c are received by receivers 51–58, and based on this, the information that the vertical checks a, b, c exist is outputted from the check presence detection unit 45, and the vertical check detection of the neck and finish portion 1 is carried out continuously and at many points as the glass bottle 3 rotates. That is, the existence of vertical checks a, b, c at the neck and finish portion 1 of the glass bottle 3 can be detected at many points at in a single operation.

By the way, the light emitting direction of emitting light L from emitters 21–32 is directed to the outer surface of the neck and finish portion and the emitting light L is converged to one place S, but the invention is able to be embodied by directing the light emitting direction of emitting light L to the vicinity of the inner surface of the neck and finish portion. In addition, emitters and receivers may be arranged as required in accord with the types of checks. In the above-mentioned embodiment, vertical checks are detected, but in this invention, checks other than vertical checks can be optionally detected by varying the setting patterns.

Figure 9:
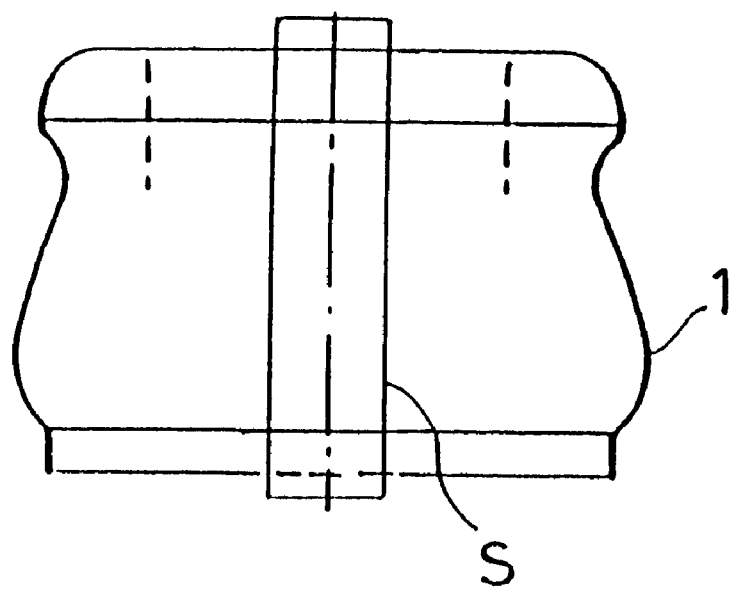
FIG. 9 is a block diagram showing a first variation example of the glass bottle neck and finish portion which can be detected in this invention.
Figure 10:
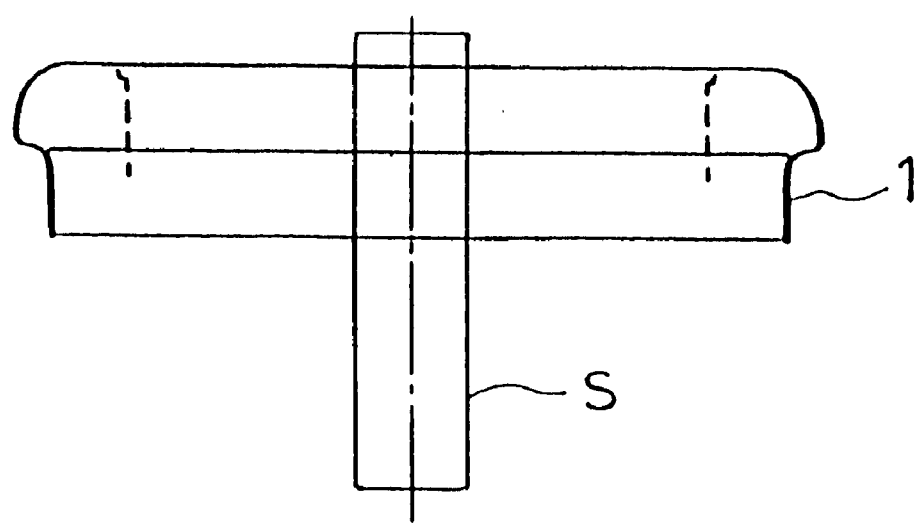
FIG. 10 is a block diagram showing a second variation example of the glass bottle neck and finish portion which can be detected in this invention.
Figure 11:
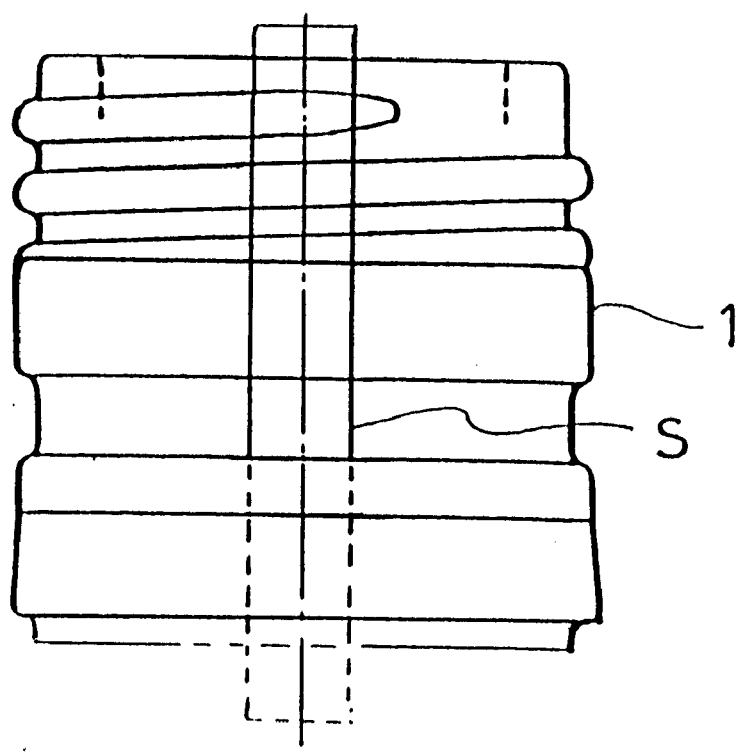
FIG. 11 is a block diagram showing a third variation example of the glass bottle neck and finish portion which can be detected in this invention.
Figure 12:
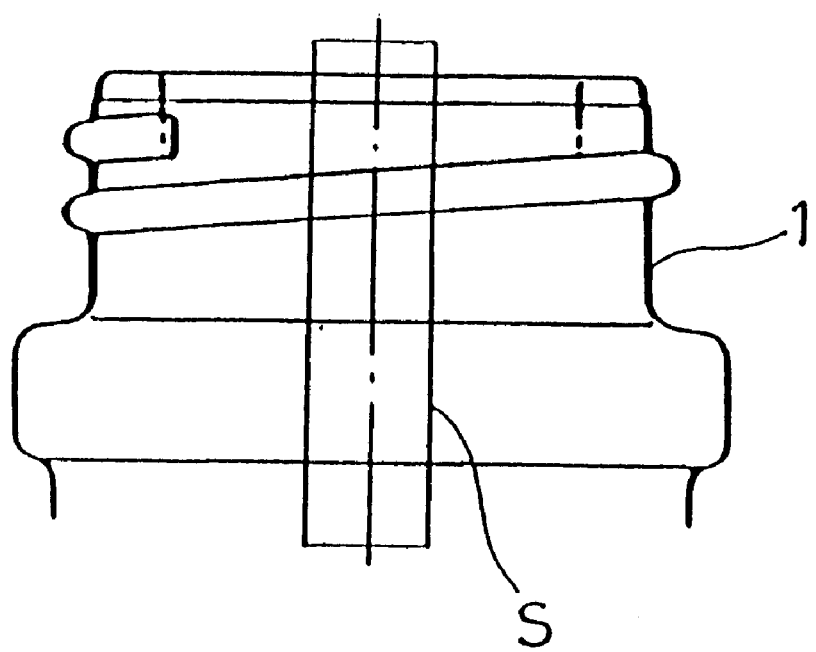
FIG. 12 is a block diagram showing a fourth variation example of the glass bottle neck and finish portion which can be detected in this invention.
Figure 13:
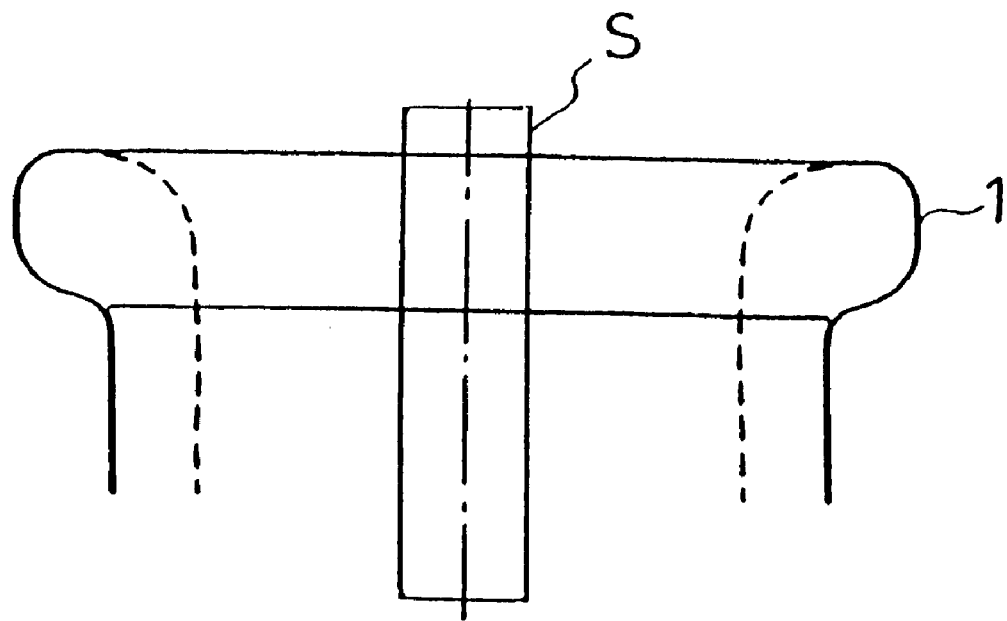
FIG. 13 is a block diagram showing a fifth variation example of the glass bottle neck and finish portion which can be detected in this invention.

The neck and finish portion of the inspected subject can be applied to the neck and finish portions of profiles shown in FIG. 9–FIG. 13. FIG. 9 shows a crown cap neck, FIG. 10 a lip neck, FIG. 11 a deep neck for pilfer proof caps, FIG. 12 a stopper neck, and FIG. 13 a cork neck, respectively. In FIG. 8–FIG. 13, character S designates a rectangular emitted region as described above.

Referring now FIG. 14–FIG. 16, the data collection processing mechanism containing the check presence detection unit 45 and light receiver control section 47 and a light emitting mechanism containing the light emitter control section 46 will be briefly described as follows.

Figure 14:
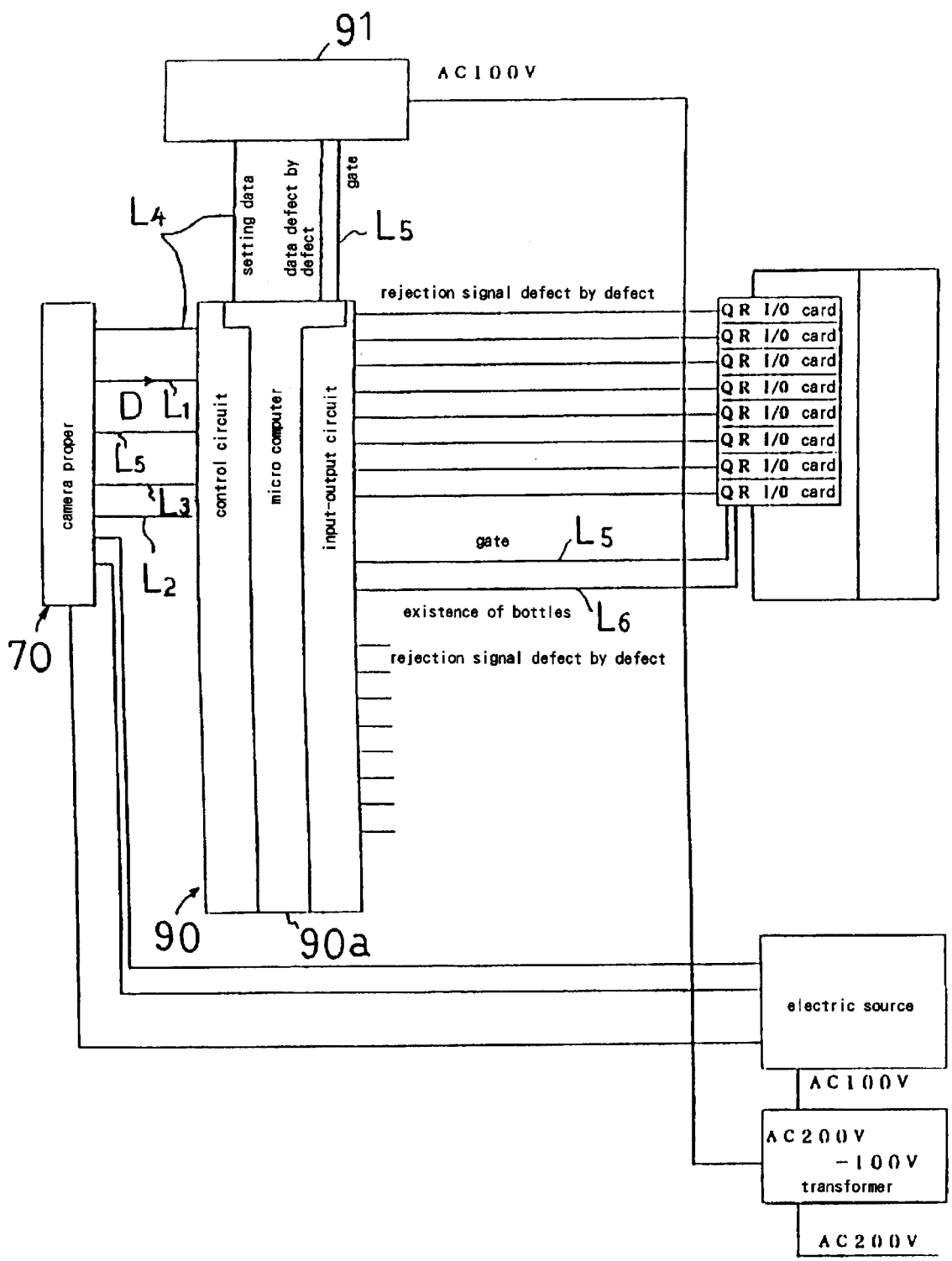
FIG. 14 is a block diagram showing a camera proper and data processor in this invention.

In FIG. 14, numeral 70 designates a camera proper and creates detection data D based on the data $D_1$, $D_2$, $D_3$ detected by 8 pieces of light receivers 51–58. Numeral 90 designates a data processor and sorts all the detection data D at the stage where the detection data D is summarized. And during detection, the camera proper 70 only operates. After completion of detection, all the detection data D is absorbed into the data processor 90 and stored in a memory. The detection data D is outputted to the data processor 90 from the camera proper 70 via the detection data line $L_1$ as 8-bit data. And at the data processor 90, acceptance or rejection of the glass bottle neck and finish portion 1 is performed, and the results are displayed on the detection monitor screen of the personal computer 91.

In this personal computer 91, checks are filed in advance by types. For example, the column of presence of upper vertical check a, middle vertical check b, and lower vertical check c generated at the upper, middle, and lower positions of the glass bottle neck and finish portion 1 in that order are displayed on the detection monitor screen by calling the file for vertical checks.

Collation of the detection data D sent from the personal computer 91 to the controller 90a with the mask data M created in advance in accord with the types of glass bottle 3 of the inspected subject is carried out by the masking operation from the detection monitor screen.

Figure 15:
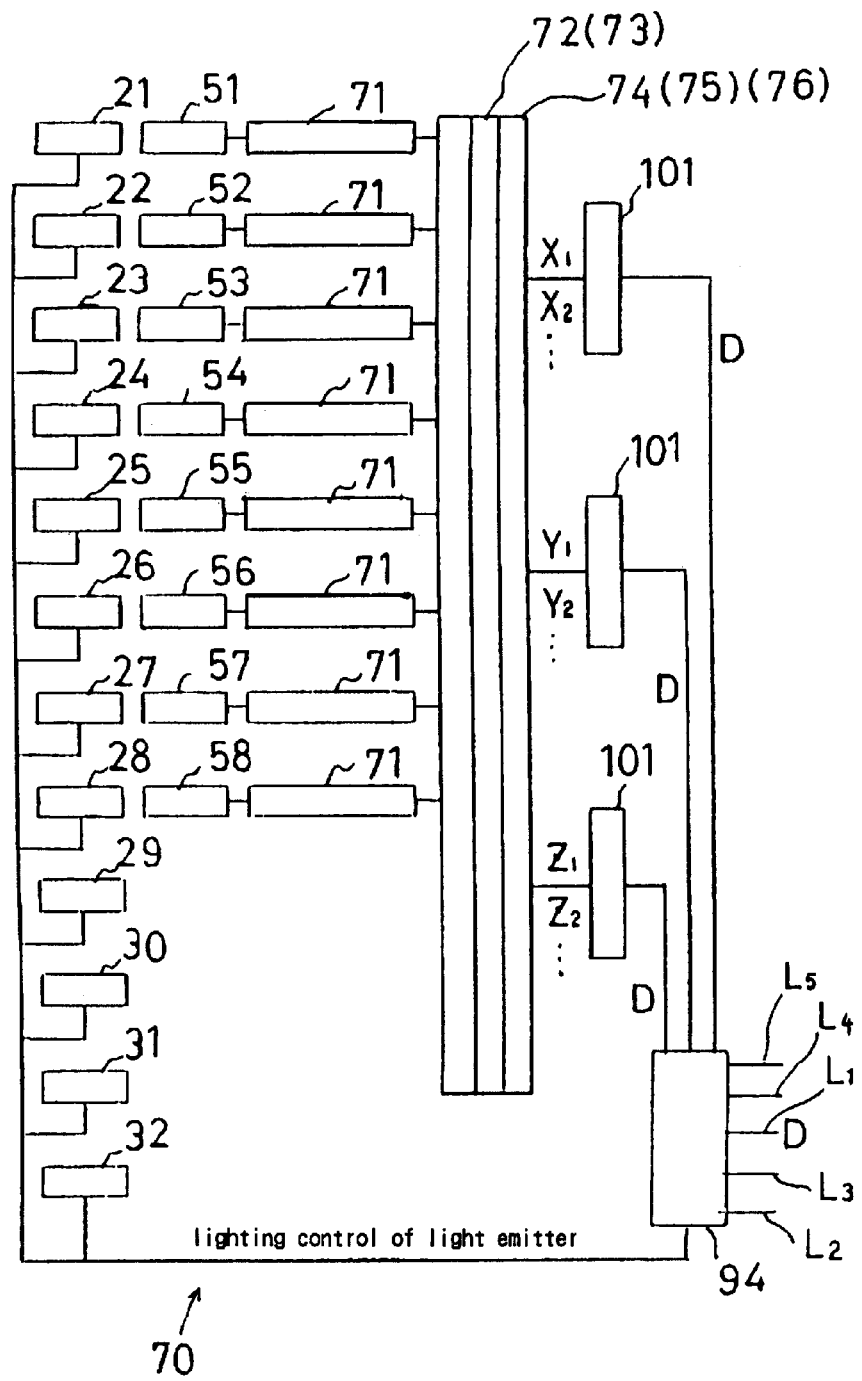
FIG. 15 is a block diagram showing the camera proper in this invention.

FIG. 15 shows the overall configuration of the camera proper 70. In FIG. 16, of the 8 light receivers 51–58 (camera 1–camera 8) as a diode array camera which is one of the composing elements of the camera proper 70, for example, a delivery route of the data caught by the light receiving sensor 2 mounted at, for example, the receiver 53 is shown.

Figure 16:
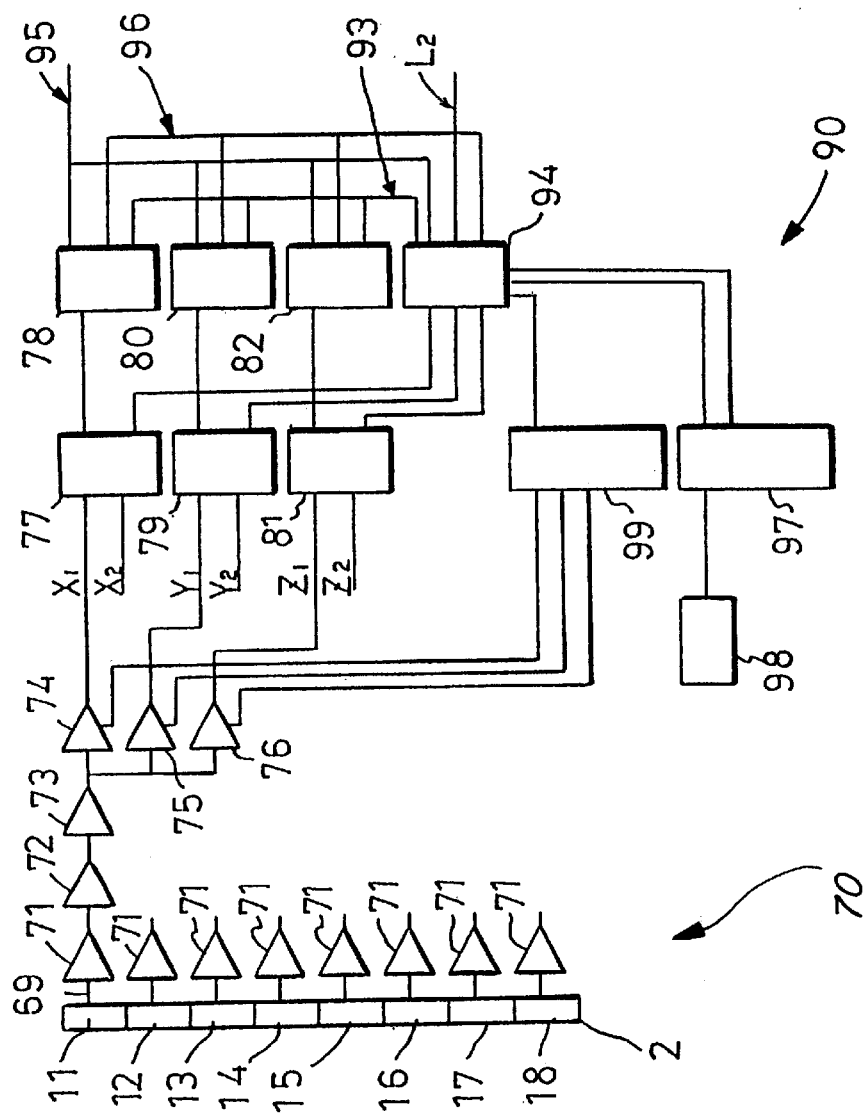
FIG. 16 is a block diagram showing an essential portion of the camera proper in this invention.

In FIG. 16, numeral 69 is a signal line of the light receiving element 11. The light receiving element 11 is one of the eight light receiving elements 11–18 composing the light receiving sensor 2 of the light receiver 53.

To the signal line 69, PRE AMP (8 channels) 71 and analog-system signal processing mechanism [for example, high pass filter (8 channels) 72, low pass filter (8 channels) 73, comparators 74, 75, 76] are equipped. If any of vertical checks a, b, c is generated in the neck and finish portion 1, current output (data signal) $D_1$ in proportion to the reflected lights A, B, C reflected at vertical checks a, b, c is outputted to the signal line 69. In such event, because all the light receivers 51–58 are constantly operated in the light emitting condition, current output (data signal) $D_2$ in proportion to the reflected light reflected at the molds seam formed at the neck and finish portion 1 as well as current output (data signal) $D_3$ in proportion to direct light transmitting through the neck and finish portion 1 are also outputted to the signal line 69.

After the data signals are properly amplified and wave-shaped by the PRE AMP 71, the data signals $D_1$, $D_2$, $D_3$ (hereinafter called simply the "detection data") passing the high pass filter 72 and the low pass filter 73 are sent out to three comparators 74, 75, 76, respectively, in one set.

From the comparator 74, non-defective signal (blue signal) $X_1$ (which corresponds to detection data) which indicates not defective is sent out to the main memory section 78 when the signals are temporarily stored in memory at the pre-memory section 77 and collected. From the comparator 75, defective signal (yellow signal) $Y_1$ (which corresponds to detection data) is sent out to the main memory section 80 when the signals are temporarily stored in memory at the pre-memory section 79 and collected. Furthermore, from the comparator 76, defective signal (red signal) $Z_1$ (which corresponds to the detection data) subject to reflected light with stronger light quantity than that of the defective signal $Y_1$ is sent out to the main memory section 82 when the signals are temporarily stored in memory at the pre-memory section 81 and collected.

The pre-memory sections 77, 79, 81 are to temporarily store the first detection data by turning on timing clocks $a_1$–$a_{12}$ from the emitters 21–32 until the second detection is carried out by turning on timing clocks $b_1$–$b_{12}$ from the emitters 21–32 shown in FIG. 15. Thereafter, the neck and finish portion 1 of the glass bottle 3 is continuously emitted with emitting light L with care to eliminate no unemitted portion in the neck and finish portion 1 of the glass bottle 3 passing the emitted region S, and the third detection data by emitters 21–32, fourth detection data . . . are temporarily stored successively in pre-memory portions 77, 79, 81. The detection data shall be collected throughout at least one circumference of the neck and finish portion 1 of the glass bottle 3. In FIG. 15, numeral 101 is a logic circuit.

Because eight emitters 51–58 are all constantly operated as described above, if, for example, in the second detection, timing clock $b_1$ from, for example, the emitter 21 comes to the eight receivers 51–58, on the receivers 51–58 side, detection data ($X_1$, $Y_1$, $Z_1$, $X_2$, $Y_2$, $Z_2$, ~$X_{64}$, $Y_{64}$, $Z_{64}$) of 8 (number of receivers)×8 (number of light receiving element)×3 (number of comparators) are temporarily stored in the pre-memory sections 77, 79, 81, and thereafter, the detection data in a lump is stored in the main memory sections 78, 80, 82. Then, when the timing clock $b_2$ comes from the emitter 22, 8×8×3 pieces of data are temporarily stored in a lump at locations with different addresses of the pre-memory portion 77, 79, and 81. This operation is carried out up to the twelfth emitter 32 and the second detection by turning on timing clocks $b_1$–$b_{12}$ is completely finished.

The detection data of 64×12 (number of emitters)×3 (number of comparators) obtained by the second detection is collated with the first detection data by turning on timing clocks $a_1$–$a_{12}$ in main memory sections 78, 80, 82, and both detection data are totaled and stored in memory. In short, the main memory sections 78, 80, 82 are constructed with OR circuits. Thereafter, in the similar manner, the third detection data is collated with the first and the second detection data at the main memory sections 78, 80, 82. And by totaling the first detection date and, the second detection date, the third detection data is also stored in memory at the main memory section 78, 80, 82. Thereafter, in the similar operation, the data is collected and processed throughout the one circumference of the neck portion 1 of the glass bottle 3.

By the way, in FIG. 16, numeral 93 designates a control signal bus and is equipped between the main logic circuit 94 and main memory sections 78, 80, 82. In this control signal bus 93, a request for read/write control data is made to the main memory sections 78, 80, 82. And between the main logic circuit 94 and the microcomputer (see FIG. 14) 92, a logic control signal line $L_2$ is equipped. Numeral 95 designates a data bus, 96 an address bus, 99 a DA converter, and 98 a light emitter driver driven by the driving means 97, and the power of the turning on timing clocks $a_1$–$a_{12}$, $b_1$–$b_{12}$ . . . and emitters 21–32 is controlled by the main logic circuit 94. In FIG. 14 and FIG. 15, character $L_3$ designates a reference clock line, character $L_4$ designates a set data line of the detection condition, character Ls designates a gate, and character $L_6$ designates a line for confirming presence of a glass bottle at the time of detection.

Under the above configuration, detection results are displayed in blue, yellow, and red colors on the monitor screen, but if a defective glass bottle with an apparent check at the glass bottle neck and finish portion 1 is inspected as a sample, and as a result, the data actually indicated in blue is displayed on the detection monitor screen though yellow or red color must be displayed on the detection monitor screen, investigation on whether to change the sensitivity or not can be carried out. Needless to say, if the non-defective sample is judged defective, the need for sensitivity adjustment is questioned, thereby improving maintenance.

As described above, in this invention, a plurality of emitters and a plurality of receivers are arranged in accord with the types of checks generated in the neck and finish portion of the glass bottle, but since each of the light receiving sensors of receivers is composed with diode arrays comprising a plurality of light receiving elements divided in advance to correspond to the vertical position of the neck and finish portion while allowing the emitting light by a plurality of emitters to be converged to one emitted region, even the contents of the check can be identified and detected at many places at a stretch at one position.

In this invention, since a successive light emitting system is adopted in place of the simultaneous light emitting system for the light turning on timing of emitting light by emitters, the data inputted as the reflected light reflected at the molds seam formed at the neck and finish portion and the data inputted as direct light transmitting through the neck and finish portion are deleted, and the light receiving surface of the light receiving sensor is composed with the divided light receiving element, both detection ratio and defective disposal ratio can be improved with the noise region reduced.

What is claimed is:

1. A check detector for a glass bottle neck and finish portion comprising:
    a bottle rotating means for rotating a glass bottle successively conveyed to a fixed position in the course of a glass bottle handing route;
    a slide block which can change position freely in the width direction and vertical direction of the handling route;
    a plurality of light emitters for emitting to the neck and finish portion of the glass bottle rotated at the fixed position, light mounted to the slide block, while the emitted region of the emitting light by the plurality of the light emitters is fixed to one position and the relevant emitting light is converged to the emitted region from directions which differ from one another;
    a plurality of light receivers equipped with light receiving sensors for detecting the reflected light reflected at any checks generated at the neck and finish portion, the reflected light reflected at the mold seam formed at the neck and finish portion, and direct light transmitted through the neck and finish portion;
    a light emitter control section for switching on a plurality of the light emitters successively and repeatedly in a light emitting condition;
    a light receiver control section for constantly operating a plurality of light receivers during the light emitting condition so that each of the reflected lights and direct light are inputted as data; and,
    control means for processing the data to eliminate the data generated by the light reflected at the mold seam and the direct light transmitted through the neck and finish portion wherein each of the light receiving sensors is composed with diode arrays comprising a plurality of light receiving elements divided in advance so as to correspond to the vertical position of the neck and finish portion and at the same time, the data inputted as reflected light reflected at the seam and the data inputted as the direct light transmitting through the neck and finish portion are subsequently deleted, respectively.

2. The check detector for the glass bottle neck and finish portion according to claim 1, wherein the emitting light is repeatedly emitted in a rectangular shaped pattern to the emitted region from a plurality of directions which differ one from another until a glass bottle makes one rotation.

3. A check detector for glass bottle neck and finish portion according to claim 2, wherein the light emitter control section switches on a plurality of light emitters successively one by one and repeatedly.

4. The check detector for the glass neck and finish portion according to claim 1, wherein mask data for deleting the data inputted as reflected light reflected at the mold seam and the data inputted as the direct light transmitted through the neck and finish portion, respectively, is created in advance and stored and a masking operation is enabled from a detection monitor screen by the control means.

5. The check detector for glass neck and finish portion according to claim 4, wherein the same cycle of the emitting light by light emitters is set for all the light emitters and at the same time the phase of the emitting light is varied for all the light emitters so that the data inputted in the light receivers can be selected.

6. The check detector for glass neck and finish portion according to claim 5, wherein the light receiving element is divided into 8 parts to enable 8-bit data processing so that the defect location of the glass bottle neck and finish portion is able to be detected still more accurately.

7. A flaw detection assembly for inspecting the production of bottles, comprising:
    rotating means for rotating an individual bottle, about a predetermined position;
    an array of light emitters positioned about the rotating means and directing light toward the predetermined position so that light can impact a bottle;
    an array of light detectors positioned about the rotating means for detecting the light emitted from the array of light emitters after impacting a bottle;
    a controller for sequentially activating the light detectors to provide data on the light contracting a flaw associated with the bottle, the light directly transmitted through the bottle and the light reflected from a known and acceptable characteristic of the bottle including seams; and
    means for removing the data on the light contacting a flaw from the remaining data to enable a flow detection signal when the removed data is compared to a predetermined value to indicate a flaw.

8. A check detector system for monitoring the production of molded glass bottle necks and finish portions comprising:
    a bottle rotating means for rotating a molded glass bottle successively conveyed to a fixed position in the course of a glass bottle handling route;
    a plurality of light emitters mounted adjacent the fixed position, for emitting, to the neck and finish portion of the glass bottle rotated at the fixed position light, while the emitted region of the emitting light by the plurality of the light emitters is fixed to one position and the relevant emitting light is converged to the emitted region from directions which differ from one another;
    a plurality of light receivers equipped with light receiving sensors for detecting the reflected light by any checks generated at the neck and finish portion, the reflected light reflected at the mold seam formed at the neck and finish portion, and direct light transmitted through the neck and finish portion; and
    a controller having a light emitter control section for switching on a plurality of the light emitters successively and repeatedly in a light emitting condition, a light receiver control section for constantly operating a plurality of light receivers during the light emitting condition so that each of the reflected lights and direct light are inputted as data, and means for processing the data to eliminate the data generated by the light reflected at the mold seam and the direct light transmitted through the neck and finish portion.

9. A check detector system according to claim 8 wherein the means for processing the data includes a memory for storing predetermined mask data representative of the reflected light at the mold seam and the direct light transmitted through the neck and finish portion and a masking operation is performed by superimposing the mask data on collected data from the light receiver control section.

10. A check detector system according to claim 9 wherein the light receivers are divided into arrays of eight light receivers each and a data bus transmits the output data in parallel to a processor within the means for processing.

11. A check detector system according to claim 10 further including a first image forming unit to shape the collective output of each light emitter into a superimposed rectangular region on the glass bottle neck and finish portion under inspection and a second image forming unit to shape the output of light from the glass bottle neck and finish portion under inspection into a rectangular configuration as applied onto the light receivers.

12. A method of inspecting glass bottles that are molded with a neck portion and a mold seam, comprising the steps of:

delivering a molded glass bottle to an inspection position;

illuminating the molded glass bottle with light of a wavelength that can be reflected by defective regions of the glass bottle;

receiving collectively any light which has been reflected by a defective region, light which has been reflected by the mold seam and light which has been transmitted through the molded glass bottle and providing an output data signal;

providing masking data representative of pre-stored output data of light which has been reflected by the mold seam and light which has been transmitted through the glass bottle of an equivalent properly manufactured glass bottle, and processing the output data signal and the pre-stored output data to mask the light which has been reflected by the mold seam of the molded glass bottle at the inspection position and the light transmitted through the molded glass bottle whereby a defect can be detected from the masked output data signal.

\* \* \* \* \*